US012616450B2

(12) United States Patent
Zhuang et al.

(10) Patent No.: US 12,616,450 B2
(45) Date of Patent: May 5, 2026

(54) PANORAMIC IMAGING IN 2D AND 3D ULTRASOUND IMAGES

(71) Applicant: FUJIFILM SonoSite, Inc., Bothell, WA (US)

(72) Inventors: Bo Zhuang, Redmond, WA (US); Yong Zhou, Woodinville, WA (US); Jean Tsou, Seattle, WA (US)

(73) Assignee: FUJIFILM SonoSite, Inc., Bothell, WA (US)

( * ) Notice: Subject to any disclaimer, the term of this patent is extended or adjusted under 35 U.S.C. 154(b) by 0 days.

(21) Appl. No.: 18/659,255

(22) Filed: May 9, 2024

(65) Prior Publication Data

US 2025/0345041 A1 Nov. 13, 2025

(51) Int. Cl.
*A61B 8/00* (2006.01)

(52) U.S. Cl.
CPC .............. *A61B 8/5246* (2013.01); *A61B 8/42* (2013.01); *A61B 8/4254* (2013.01); *A61B 8/463* (2013.01); *A61B 8/483* (2013.01)

(58) Field of Classification Search
CPC ....... A61B 8/5246; A61B 8/42; A61B 8/4254; A61B 8/463; A61B 8/483
See application file for complete search history.

(56) References Cited

U.S. PATENT DOCUMENTS

| | | | |
|---|---|---|---|
| 5,782,766 | A | 7/1998 | Lee et al. |
| 6,416,477 | B1 | 7/2002 | Jago et al. |
| 9,642,601 | B2 | 5/2017 | Shin et al. |
| 10,130,328 | B2 | 11/2018 | De Beni et al. |
| 10,219,784 | B2 | 3/2019 | Lee et al. |
| 10,426,345 | B2 | 10/2019 | Shekhar et al. |
| 11,386,606 | B2 | 7/2022 | Mory et al. |
| 11,647,987 | B2 | 5/2023 | Hung et al. |
| 2018/0132724 | A1* | 5/2018 | Waechter-Stehle .......................... A61B 8/4218 |
| 2018/0271484 | A1* | 9/2018 | Whisler ............... A61B 8/0825 |
| 2019/0125301 | A1* | 5/2019 | Jago ....................... A61B 8/463 |
| 2019/0388063 | A1* | 12/2019 | Oka ........................ A61B 8/461 |
| 2020/0069291 | A1* | 3/2020 | Zaslavsky ............ A61B 8/4245 |
| 2020/0411165 | A1* | 12/2020 | Torii ........................ G06T 11/60 |
| 2021/0204906 | A1 | 7/2021 | Giphart et al. |

OTHER PUBLICATIONS

"Endoscopic Ultrasound—Aloka Arietta 850", Retrieved at: https://medical.olympusamerica.com/products/premium-ultrasound-processor-arietta850—on Jan. 3, 2024, 5 pages.

* cited by examiner

*Primary Examiner* — Brooke Lyn Klein
(74) *Attorney, Agent, or Firm* — Colby Nipper PLLC

(57) ABSTRACT

Systems and methods for panoramic imaging in 2D and 3D ultrasound imaging are disclosed. The techniques disclosed herein use image registration to combine the 2D images into a 3D volume. Ultrasound images collected in different locations are combined using image tracking. When the transducer moves along a lateral direction (in line with a longitudinal axis of the transducer), a portion of the image is overlapped between frames and the overlapping frames can be patched. When the transducer moves along an elevational direction (non-parallel to the longitudinal axis of the transducer), there is no overlap between frames and the non-overlapping frames are not patched together but are stored side-by-side to create a volume. The storage and patching processes can be adaptive (e.g., the images are not stored or patched if there is minimal difference between neighboring frames).

20 Claims, 11 Drawing Sheets

100

100

200

400

600

700

900

950

1000

PANORAMIC IMAGING IN 2D AND 3D ULTRASOUND IMAGES

BACKGROUND

Anatomical structures are three dimensional, whereas ultrasound imaging generally produces two-dimensional images. In some cases, it may be desirable to acquire ultrasound volume for three-dimensional (3D) imaging; however, it is challenging to acquire ultrasound volume in 3D based on a collection of two-dimensional (2D) images. Generally, 3D-ultrasound devices are expensive to manufacture or have undesirable resolution and/or signal-to-noise ratio (SNR). One-dimensional (1D)-array transducers are common in ultrasound systems and can produce high-resolution 2D images. However, such 1D-array transducers must be mechanically or manually operated and moved to acquire 3D-volume data. Mechanically moved 1D-array transducers are generally expensive and have a limited field of view (FOV). Manually moved 1D-array transducers generally result in poor quality of acquired volume due to inconsistent and/or unsteady movement by the user. In addition, the existence of bone structures and their specular-reflector behavior can limit the performance of the transducer in acquiring ultrasound data under bone surfaces.

Using a 2D-array transducer can be cost prohibitive for many users and have a limited FOV compared with a moving 1D-array transducer. The limitations in these conventional techniques can lead to a poor user experience and sub-optimal imaging results.

SUMMARY

Systems and methods for panoramic imaging in 2D and 3D ultrasound imaging are disclosed. The techniques disclosed herein use image registration to combine 2D ultrasound images into a 3D volume. Ultrasound images collected in different locations are combined using image tracking. When the transducer moves along a lateral direction (aligned with a longitudinal axis of the transducer), a portion of the anatomy is overlapped between frames and the overlapping frames can be patched together. When the transducer moves along an elevational direction (non-parallel to the longitudinal axis of the transducer), there is no overlap between frames and the non-overlapping frames are not patched together but are stored side-by-side to create a volume. The storage and patching processes can be adaptive (e.g., the images are not stored or patched if there is minimal difference between neighboring frames).

In one implementation of the 3D-volume data acquisition disclosed herein, the transducer moves along the elevational direction first and then the lateral direction. A first indicator (e.g., visual message, audio signal) can be provided to the user to notify the user of a low correlation between 2D images being generated (e.g., neighboring frames cannot be patched). A second indicator (e.g., green icon) can be provided to notify the user of a high correlation between 2D images being generated (e.g., neighboring frames can be patched together). This procedure can be repeated for multiple sweeps of the transducer.

In aspects, an ultrasound system is disclosed. The ultrasound system includes an ultrasound scanner, a guidance controller, one or more processors, and one or more computer-readable storage media. The ultrasound scanner is configured to generate ultrasound data based on reflections of ultrasound signals transmitted by the ultrasound scanner at an anatomy of a patient. In implementations, the ultrasound scanner includes a transducer having a width and a length, where the length is greater than the width. The transducer has a first axis along the length, a second axis along the width, and a third axis in an axial direction of the transducer. The guidance controller is configured to provide guidance instructions to guide a user to manually move the ultrasound scanner in a sweep pattern over a surface area of the patient. The sweep pattern includes lateral movement and elevational movement of the ultrasound scanner. The lateral movement is defined as movement of the ultrasound scanner in a lateral direction that is in substantially parallel to the first axis of the transducer. The elevational movement is defined as movement of the ultrasound scanner in an elevational direction that is substantially parallel to the second axis. The one or more computer-readable storage media include instructions stored thereon that, responsive to execution by the one or more processors, cause the one or more processors to generate a plurality of two-dimensional (2D) ultrasound images based on the ultrasound data generated over the sweep pattern and combine the plurality of 2D ultrasound images into a 3D volume using image registration.

In aspects, a method is disclosed. The method includes receiving ultrasound data generated by an ultrasound scanner based on reflections of ultrasound signals transmitted by the ultrasound scanner at an anatomy of a patient. The method also includes receiving tracking information corresponding to one or more parameters associated with the ultrasound scanner, the one or more parameters defined when the ultrasound signals are transmitted by the ultrasound scanner. In addition, the method includes generating ultrasound image frames based on the ultrasound data. Further, the method includes providing guidance information to guide a user in manually moving the ultrasound scanner in one or more sweep patterns that cover a surface area of the patient, the guidance information including instructions for moving the ultrasound scanner in different directions over the one or more sweep patterns. Also, the method includes using image registration to combine the ultrasound image frames into a three-dimensional (3D) volume for display, the image registration including the tracking information.

BRIEF DESCRIPTION OF THE DRAWINGS

The appended drawings illustrate examples and are, therefore, exemplary embodiments and not considered to be limiting in scope.

DETAILED DESCRIPTION

Figure 1:
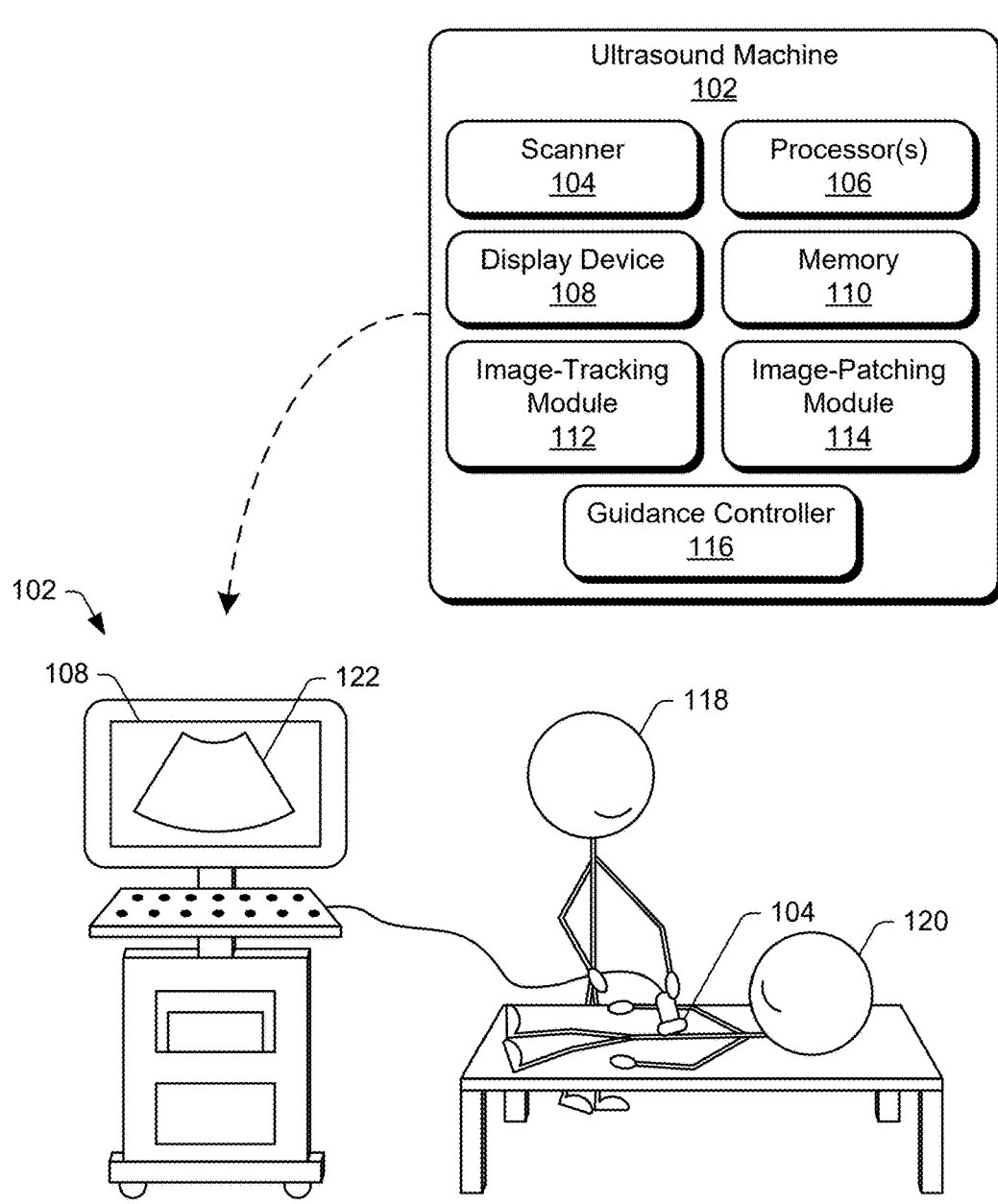
FIG. 1 illustrates an example environment for an ultrasound system having an ultrasound scanner, in accordance with one or more implementations.

A conventional 3D-ultrasound imaging system requires a 2D-phased array or a mechanically moved 1D-array transducer. The introduction of these devices increases the cost of the system. An alternative technique uses a 1D-array transducer with unguided manual movement. However, the resulting volume can have limited quality because it is challenging for a user to maintain a constant speed of manual motion of the transducer along with a constant compression force on the transducer (e.g., pressed against the patient's skin), particularly when the patient is moving (e.g., breathing). This unguided manual approach can produce an output volume that is distorted, blurred, or includes gaps.

The techniques disclosed herein provide a guided way for the user to manually operate a scanner to acquire ultrasound data sufficient to create a 3D volume. This guided technique can be implemented using a common 1D-array transducer and without integrating expensive sensors and/or mechanical apparatuses. The guided technique can instruct the user on when to start moving the scanner and in which direction over the patient, when to stop moving the scanner, when to turn the scanner to move the scanner in a new direction, etc. After the ultrasound data is acquired, the ultrasound system can use image registration to combine the collected ultrasound data or ultrasound images generated from the ultrasound data into a 3D volume, which can be rendered via a display device for the user.

During the data acquisition, parameters of the scanner are tracked. For example, spatial positioning, acceleration, angle, and elevation of the scanner or the transducer of the scanner can be tracked and correlated to multiple pixels (including all pixels) in each ultrasound image produced by the acquired ultrasound data. By tracking such parameters of the scanner, the ultrasound system can patch overlapping ultrasound images together to form panoramic images and store non-overlapping ultrasound images side-by-side to create a volume.

Further, the guided techniques provide smart patching in which image patching is performed only on ultrasound images generated when the scanner is moving in a lateral direction to produce high-resolution images. When the scanner moves in an elevational direction, which produces low-resolution images, the image patching is not performed. Such smart patching reduces processing power and computation time. Another example of smart patching includes adaptive patching of structures under a specular reflector (e.g., bone). For example, when a bone surface is detected, the smart patching techniques automatically use the higher intensity pixels, rather than overwriting such higher intensity pixels with lower intensity shadow pixels. Such use of the higher-intensity pixels can reduce the impact from bone shadow. In some cases, the smart patching can be controlled using sensor information from one or more sensors that track the parameters of the scanner or its transducer during data acquisition.

In some aspects, the guided techniques guide the user through multiple sweep patterns. Multiple sweep patterns, each with a different orientation (e.g., rotational position) of the scanner or its transducer, can provide high-resolution ultrasound images in different directions over the same area of the patient. Using image registration, the ultrasound images from such multiple sweep patterns can be used to create a high-resolution 3D volume.

Example Ultrasound System

FIG. 1 illustrates an example environment for an ultrasound system 100 having an ultrasound scanner, in accordance with one or more implementations. Generally, the ultrasound system 100 includes an ultrasound machine 102 (e.g., ultrasound device), which generates data based on high-frequency sound waves reflecting off body structures. The ultrasound machine 102 includes various components, some of which include a scanner 104, one or more processors 106, a display device 108, and a memory 110. In aspects, the ultrasound machine 102 also includes an image-tracking module 112, an image-patching module 114, and a guidance controller 116.

A user 118 (nurse, ultrasound technician, operator, sonographer, etc.) directs the scanner 104 toward a patient 120 to non-invasively scan internal bodily structures (organs, tissues, etc.) of the patient 120 for testing, diagnostic, or therapeutic reasons. In some implementations, the scanner 104 includes an ultrasound transducer array and electronics communicatively coupled to the ultrasound transducer array to transmit ultrasound signals to the patient's anatomy and receive ultrasound signals reflected from the patient's anatomy. In some implementations, the scanner 104 is an ultrasound scanner, which can also be referred to as an ultrasound probe.

The display device 108 is coupled to the processor 106, which processes the reflected ultrasound signals to generate ultrasound data. The display device 108 is configured to generate and display an ultrasound image (e.g., ultrasound image 122) of the anatomy based on the ultrasound data generated by the processor 106 from the reflected ultrasound signals detected by the scanner 104. In some aspects, the ultrasound data includes the ultrasound image 122 or data representing the ultrasound image 122. In some aspects, the display device 108 is integrated with the scanner 104.

The image-tracking module 112 can track various information corresponding to the ultrasound images 122 (e.g., frames) generated by the scanner 104, including one or more parameters of the scanner 104 itself (spatial position, acceleration, angle, elevation, etc.) when generating each ultrasound image 122. The image-patching module 114 patches overlapping ultrasound images together. Non-overlapping ultrasound images can be stored side-by-side to produce a 3D volume. The guidance controller 116 provides instructions or signals to the user to guide the user in manually moving the transducer in one or more sweeping patterns to collect ultrasound data sufficient to produce the 3D volume of ultrasound data and avoid gaps (missing portions) in the data.

Figure 2:
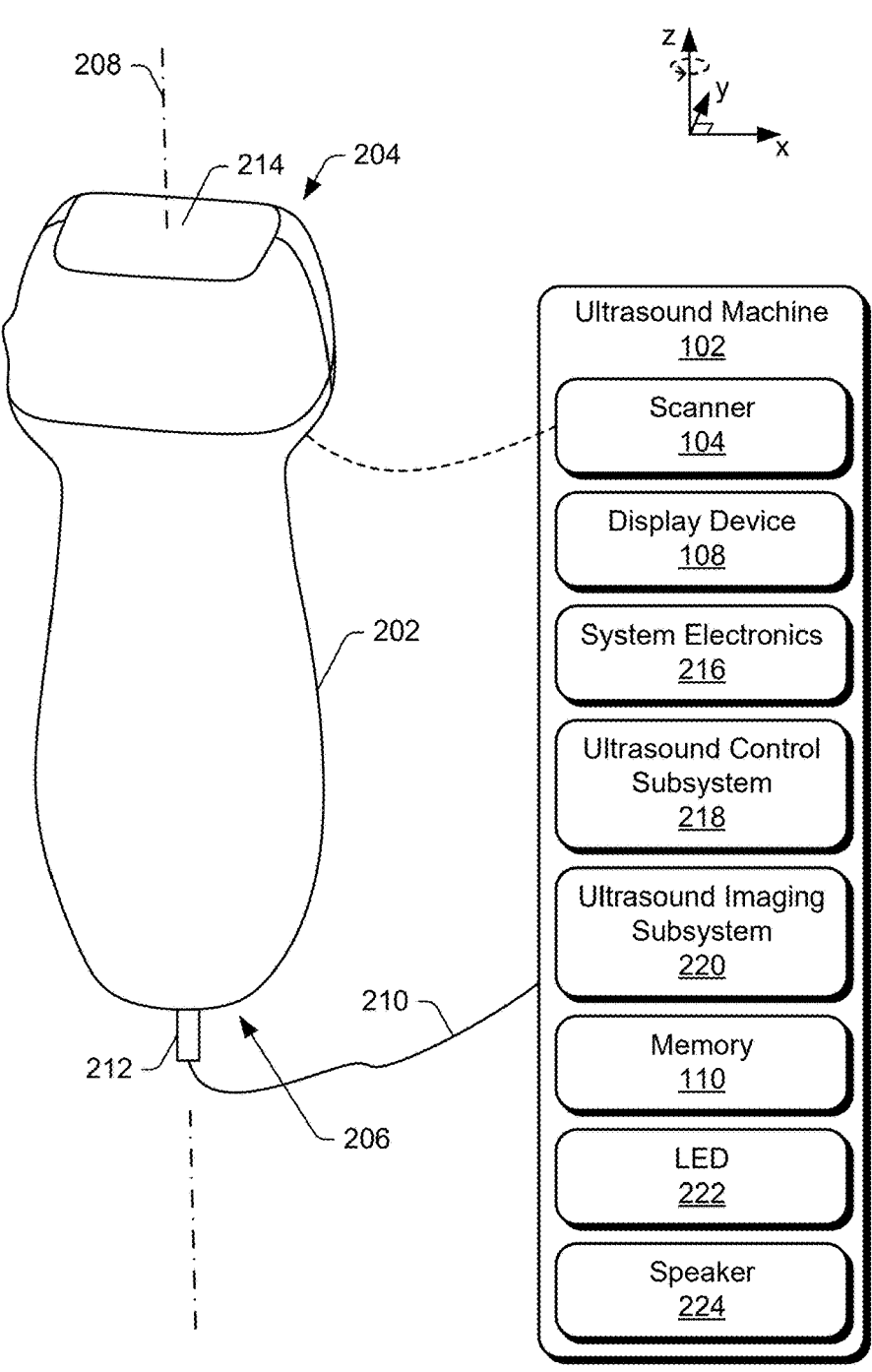
FIG. 2 illustrates an example implementation of the ultrasound scanner from FIG. 1.

FIG. 2 illustrates an example implementation 200 of the ultrasound scanner 104 from FIG. 1. The scanner 104 (e.g., ultrasound scanner, probe) includes an enclosure 202 extending between a distal end portion 204 and a proximal end portion 206. The enclosure 202 includes a central axis 208 (e.g., longitudinal axis) that intersects the distal end portion 204 and the proximal end portion 206. The central axis 208 corresponds to an axial direction of the scanner 104. The scanner 104 is electrically coupled to an ultrasound imaging system (e.g., the ultrasound machine 102) via a cable 210 that is attached to the proximal end portion 206 of the scanner 104 by a strain-relief element 212. In some implementations, the scanner 104 is wirelessly coupled to the ultrasound imaging system and communicates with the ultrasound imaging system via one or more wireless trans-mitters, receivers, or transceivers over a wireless connection or network (Bluetooth™, Wi-Fi™, etc.).

A transducer assembly 214 (transducer 214) having one or more transducer elements is electrically coupled to system electronics 216 in the ultrasound machine 102. In operation, the transducer assembly 214 transmits ultrasound energy from the one or more transducer elements toward a subject and receives ultrasound echoes from the subject. The ultra-sound echoes are converted into electrical signals by the transducer element(s) and electrically transmitted to the system electronics 216 in the ultrasound machine 102 for processing and generation of one or more ultrasound images.

Capturing ultrasound data from a subject using a trans-ducer assembly (e.g., the transducer assembly 214) gener-ally includes generating ultrasound signals, transmitting ultrasound signals into the subject, and receiving ultrasound signals reflected by the subject. A wide range of frequencies of ultrasound can be used to capture ultrasound data, such as, for example, low-frequency ultrasound (e.g., less than 15 Megahertz (MHz)) and/or high-frequency ultrasound (e.g., greater than or equal to 15 MHz). A particular frequency range to use can readily be determined based on various factors, including, for example, depth of imaging, desired resolution, and so forth.

In some implementations, the system electronics 216 include one or more processors (e.g., the processor(s) 106 from FIG. 1), integrated circuits, application-specific inte-grated circuits (ASICs), field-programmable gate arrays (FPGAs), and power sources to support functioning of the ultrasound machine 102. In some implementations, the ultrasound machine 102 also includes an ultrasound control subsystem 218 having one or more processors. At least one processor, FPGA, or ASIC causes electrical signals to be transmitted to the transducer(s) of the scanner 104 to emit sound waves and also receives electrical pulses from the scanner 104 that were created from the returning echoes. One or more processors, FPGAs, or ASICs process the raw data associated with the received electrical pulses and form an image that is sent to an ultrasound imaging subsystem 220, which causes the image (e.g., the ultrasound image 122 in FIG. 1) to be displayed via the display device 108. Thus, the display device 108 can display ultrasound images from the ultrasound data processed by the processor(s) of the ultrasound control subsystem 218. The display device 108 can be integrated with the scanner 104 such that the display device 108 is incorporated into the enclosure 202 of the scanner 104. Alternatively, the display device 108 can be separate from the scanner 104, such as the example shown in FIG. 1.

The ultrasound machine 102 can also include one or more light sources (e.g., light-emitting diode (LED) 222) and/or one or more audio output devices (e.g., speaker 224). The LED 222 and/or the speaker 224 can be coupled to or integrated with the ultrasound machine 102, separate from the scanner 104. Alternatively, the LED 222 and/or the speaker 224 can be coupled to or integrated with the scanner 104. The LED 222 and/or the speaker 224 can be used to provide messages, indications, or instructions for the user during data acquisition using the scanner 104. For example, the user can be notified via the LED 222, the speaker 224, or both, to start movement of the transducer or to stop movement of the transducer. In another example, the user can be notified via the LED 222, the speaker 224, or both, that the ultrasound images being generated based on the current movement of the transducer have a good correlation and are thus being patched together or have a poor corre-lation and thus cannot be patched together. The LED 222 and/or the speaker 224 can also be used to instruct the user which direction to move the transducer. The instructions provided to the user via the LED 222 can be associated with at least one of color, brightness level, flash pattern, size, etc. of the LED 222. Further details and examples are described below.

In some implementations, the ultrasound machine 102 also includes one or more user input devices (a keyboard, a cursor control device, a microphone, a camera, etc.) that input data and enable taking measurements from the display device 108 of the ultrasound machine 102. The ultrasound machine 102 can also include a disk storage device (e.g., computer-readable storage medium such as read-only memory (ROM), a Flash memory, a dynamic random-access memory (DRAM), a NOR memory, a static random-access memory (SRAM), a NAND memory, and so on) for storing the acquired ultrasound images. In addition, the ultrasound machine 102 can include a printer that prints the image from the displayed data. To avoid obscuring the techniques described herein, such user input devices, disk storage device, and printer are not shown in FIG. 2.

Figure 3:
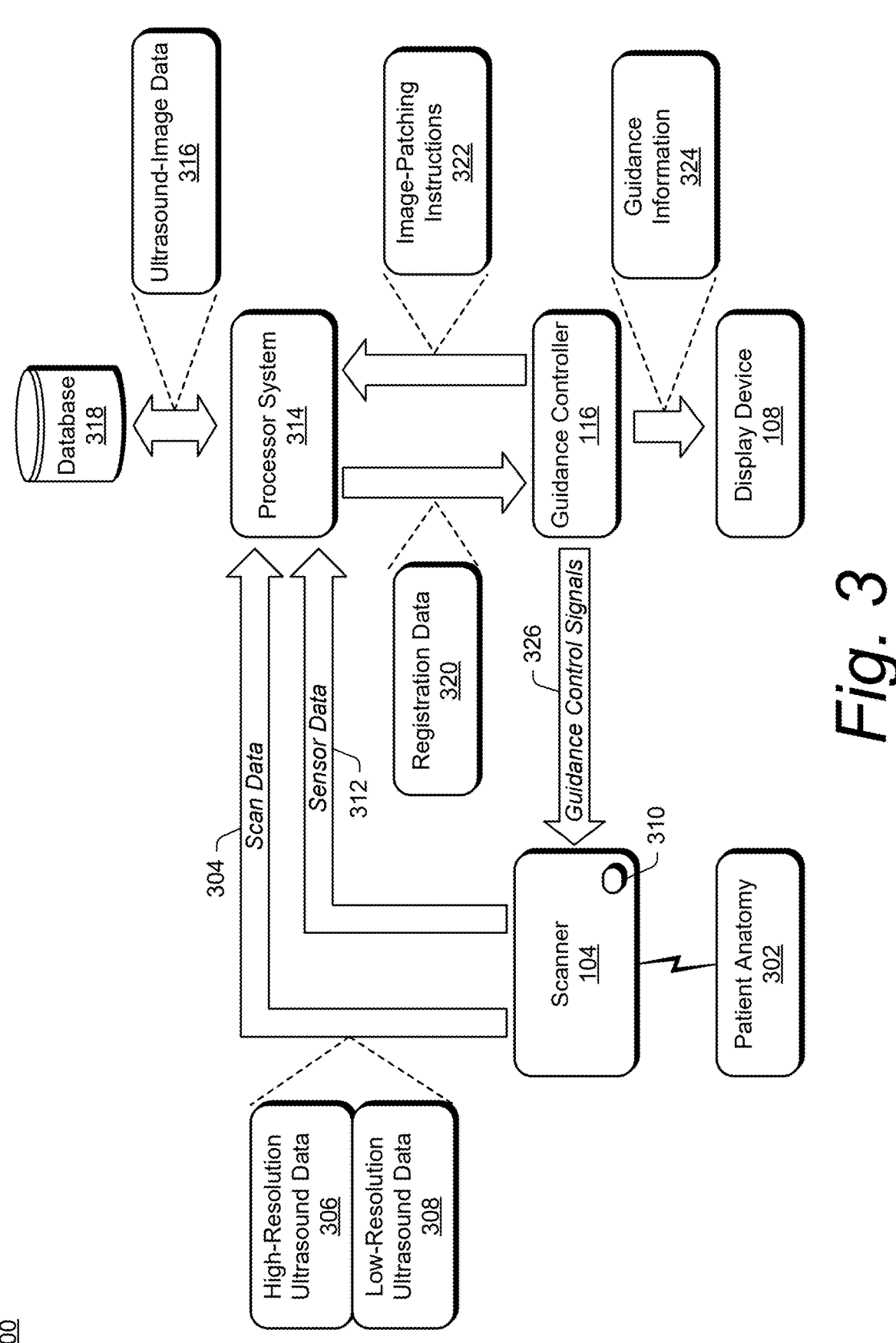
FIG. 3 illustrates an example ultrasound system for panoramic imaging in 2D and 3D ultrasound images, in accordance with one or more implementations.

FIG. 3 illustrates an example 300 of an ultrasound system (e.g., the ultrasound system 100 in FIG. 1) in accordance with one or more implementations. In aspects, the user manually holds and operates the scanner 104 to scan a patient anatomy 302. The scanner 104 generates scan data 304 from reflections of ultrasound signals transmitted by the scanner 104 at the patient anatomy 302. The user moves the scanner 104 over the surface of the patient in different directions to cover an area of the surface of the patient. Depending on the direction of movement of the scanner 104, the scanner 104 generates high-resolution ultrasound data 306 or low-resolution ultrasound data 308. As described further with respect to FIG. 4, high-resolution ultrasound data is generated when the scanner 104 is moved in a direction corresponding to a longitudinal axis of the 1D-ar-ray transducer such that a portion of the patient anatomy 302 is overlapped between consecutive frames produced from the scan data 304. Further, low-resolution ultrasound data is generated with the scanner 104 is moved a direction non-parallel to the longitudinal axis of the transducer (e.g., orthogonal to the length direction) such that neighboring frames produced by the scan data 304 do not overlap.

In some implementations, the scanner 104 includes one or more sensors 310 configured to detect one or more param-eters of the scanner 104. For example, the sensor 310 can detect one or more parameters including spatial position, acceleration, angle, elevation, etc. of the scanner 104. The sensor 310 can be an optical sensor, a magnetic sensor, a gyro sensor, etc. In some aspects, the sensor 310 can be a proportional-integral-derivative (PID) controller used to provide a control loop feedback mechanism to remove acquisition oscillation and increase process efficiency. The sensor 310 provides sensor data 312 representing the detected parameter(s) of the scanner 104.

The scan data 304 is transmitted to a processor system 314 (e.g., processors 106, processors of the system electronics 216, processors of the ultrasound control subsystem 218). In some aspects, the sensor data 312 is also sent to the processor system 314. The processor system 314 processes the scan data 304 and, in some cases, the sensor data 312 to generate ultrasound-image data 316. The ultrasound-image data 316 can be stored in a database 318, such as the memory 110. The processor system 314 can use the ultrasound-image data 316 to generate registration data 320.

The registration data 320 can include dimensions in a coordinate system and/or angular dimensions that define spatial positioning and movement of the scanner 104 for one or more pixels (including each pixel) in the ultrasound-image data 316. The registration data 320 can be image-based, sensor-based, or both.

The guidance controller 116 can use the registration data 320 to determine image-patching instructions 322 for the processor system 314 to patch image frames or not to patch image frames. In some implementations, the sensor 310 can trigger a patching function to cause the processor system 314 to patch image frames or to stop patching image frames.

In aspects, the guidance controller 116 can use the registration data 320 to provide guidance information 324 to the display device 108 to guide the user in moving the scanner 104 over the area of the patient in a manner that covers the entire area without missing a portion of the area. Such guidance information 324 can include directions for where to move the scanner 104 (arrows, text, diagram, etc.). The guidance information 324 can include an indication of whether the current movement of the scanner 104 is enabling image patching, such that the movement is within a range of movement speeds and the direction of movement is such that the images can be patched. The guidance information 324 can include an indication of whether the current movement of the scanner 104 is not enabling image patching, such that the movement is outside the range of movement speeds and/or the direction of movement is such that the images cannot be patched. These and other aspects are disclosed in more detailed below.

In some implementations, the guidance controller 116 can use the registration data 320 to provide guidance control signals 326 to the scanner 104. For example, if the scanner 104 includes a display screen (e.g., display device 108), a light source (e.g., LED 222 in FIG. 2), and/or an audio output device (e.g., speaker 224 in FIG. 2), then the guidance controller 116 can transmit guidance control signals to the scanner 104 to cause the display device 108 to provide a visual notification, to cause the LED 222 to illuminate, or to cause the speaker 224 to provide an audio signal, or both. Such display, illumination, or audio signal can be used as a message to notify the user that, as the user is moving the scanner 104, the processor system 314 is patching ultrasound images or that the processor system 314 is not patching ultrasound images. Such visual or audio indicators can also be used to guide the user in moving the scanner 104, such as to move the scanner 104 faster, slower, in a particular direction, or to change the orientation of the scanner 104 (rotate the scanner 104, change the angle of the scanner 104, etc.). In some implementations, the speaker 224 is integrated with or coupled to the display device 108 and the guidance information includes the guidance control signals.

Figure 4:
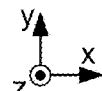
FIG. 4 illustrates an example of a transducer and a coordinate system usable for providing guidance information to the user for manual movement of the scanner.
Figure 4:
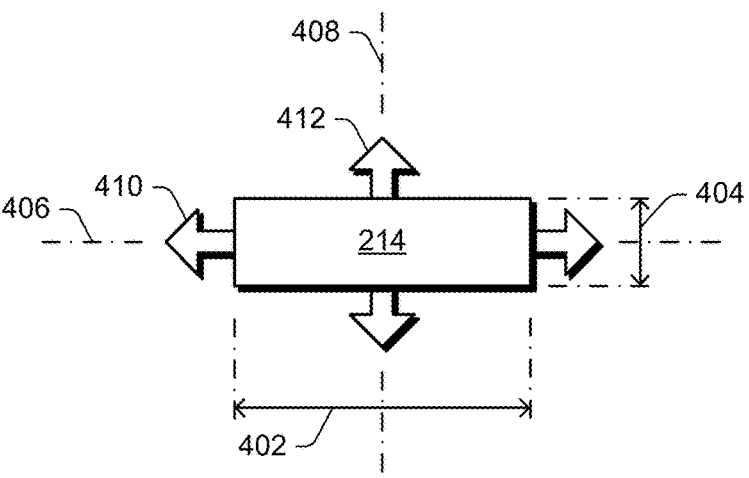

FIG. 4 illustrates an example 400 of a transducer (e.g., the transducer 214) and a coordinate system usable for providing guidance information to the user for manual movement of the scanner 104. The manual movement of the scanner 104 is disclosed herein relative to a coordinate system of the transducer 214 itself. In implementations disclosed herein, the transducer 214 is a one-dimensional array transducer commonly used in conventional freehand ultrasound imaging systems. The transducer 214 includes a length 402 and a width 404, where the length is greater than the width. Using a Cartesian coordinate system, an x-axis is aligned with the length 402 of the transducer 214 such that the x-axis corresponds to a first axis 406 (e.g., longitudinal axis) of the transducer 214. In addition, a y-axis is aligned with the width 404 of the transducer 214 such that the y-axis corresponds to a second axis 408, which is orthogonal to the first axis 406 and forms an xy-plane. Further, a z-axis is aligned with (e.g., parallel to, coaxial with) an axial direction of the scanner 104, which is directed into the page in the illustrated example 400. Accordingly, the example illustration is an abstract view of the transducer as if from the inside of the enclosure of the scanner 104 such that the transducer 214 transmits ultrasound signals in the axial direction (e.g., into the page).

As described herein, movement directions of the scanner 104 are relative to the orientation of the transducer 214 in space. For example, lateral movement is movement of the transducer 214 or the scanner 104 in a lateral direction 410, or along the first axis 406 (e.g., parallel to the length 402 of the transducer 214). Further, elevational movement is movement of the transducer 214 or the scanner 104 in an elevational direction 412, which is non-parallel to the first axis 406, or in a direction that is generally along the second axis 408.

Figure 5:
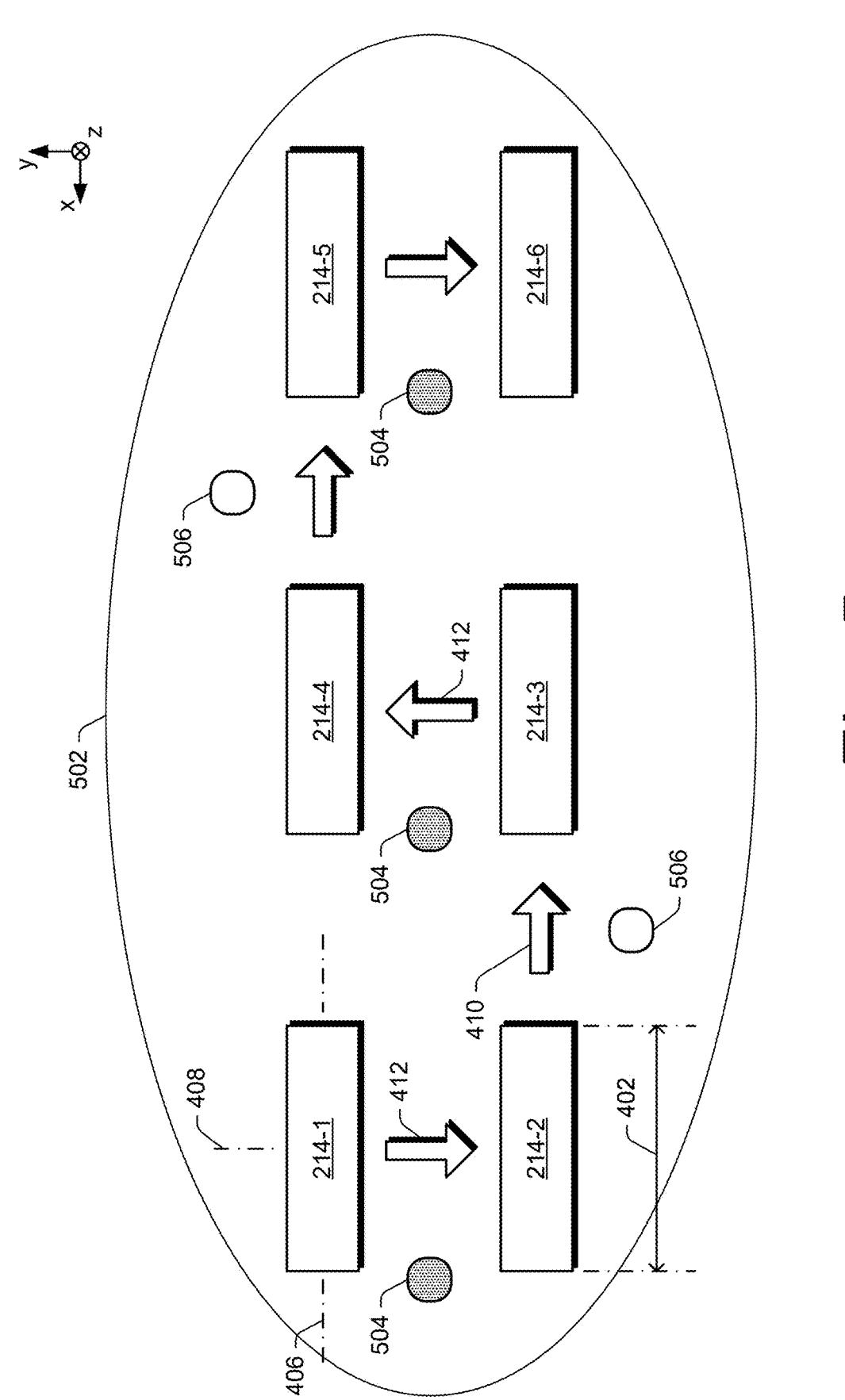
FIG. 5 illustrates an example first sweep pattern for acquisition of a 3D ultrasound volume with a 1D-array transducer using image registration.

FIG. 5 illustrates an example first sweep pattern 500 for acquisition of a 3D ultrasound volume with a 1D-array transducer using image registration. As the transducer 214 is moved to different locations over an area 502, ultrasound data is collected and used to generate ultrasound images. Ultrasound images corresponding to different locations can be combined using image registration. For example, when the transducer 214 moves along the lateral direction 410 (e.g., parallel to the first axis 406 of the transducer 214), a portion of the anatomy is overlapped between frames. Overlapping frames can be patched together. When the transducer moves along the elevation direction 412 (e.g., non-parallel to the first axis 406 of the transducer 214 or substantially parallel to the second axis 408), there is no overlap between frames. Non-overlapping frames are not patched together. Rather, non-overlapping frames can be stored side-by-side to create a volume. In some aspects, the storage and patching processes are adaptive, such that images are not stored or patched if there is minimal difference between neighboring frames (e.g., frames differ by less than a threshold value).

In the example first sweep pattern 500 for 3D-volume ultrasound-data acquisition, the transducer 214 moves along the elevational direction 412 followed by movement in the lateral direction 410. For example, the transducer begins at a first transducer position 214-1 and moves in the elevational direction 412 to a second transducer position 214-2. Then, the transducer moves in the lateral direction 410 to a third transducer position 214-3. The user then moves the transducer 214 in the elevational direction 412 from the third transducer position 214-3 to a fourth transducer position 214-4. This movement pattern can continue to a fifth transducer position 214-5, a sixth transducer position 214-6, and so on. The first sweep pattern 500 is not limited to the illustrated example and can include additional or fewer transducer positions to cover an area. Additionally, distances shown between transducer locations are exaggerated for illustrative purposes. For example, a gap between the second transducer position 214-2 and the third transducer position 214-3 can be zero, such that the transducer only moves a distance equal to or less than its length 402. This can avoid missing portions of the area 502.

When moving in the lateral direction 410, high-resolution ultrasound data is acquired and images can be patched together to provide a high-resolution panoramic image. For example, high-resolution images can be patched between the second transducer position 214-2 and the third transducer position 214-3. Additionally, if the sixth transducer position 214-6 lines up with the third transducer position 214-3 and there is some overlap between them, then an image generated from the sixth transducer position 214-6 can be patched together with the last image from the third transducer position 214-3. In this way, a high-resolution panoramic image can be generated that covers the distance from the second transducer position 214-2 to the sixth transducer position 241-6. Using image tracking and patching, another high-resolution panoramic image can be generated that covers the distance traveled from the first transducer position 214-1 to the fifth transducer position 214-5, assuming some overlap or a zero gap between the first transducer position 214-1 and the fourth transducer position 214-4.

When moving the transducer 214 in the elevational direction 412, low-resolution ultrasound data is acquired and images are not patched together. Consequently, ultrasound images generated between the first and second transducer positions 214-1, 214-2, between the third and fourth transducer positions 214-3, 214-4, and between the fifth and sixth transducer positions 214-5, 214-6 are stored side-by-side to create a volume but are not patched together. These low-resolution images have no overlap between frames due to the orientation of the 1D-array of the transducer 214.

This sweeping procedure can be repeated for multiple sweeps. Accordingly, the techniques disclosed herein can be implemented using a 1D-array transducer, rather than a complicated and expensive 2D-array transducer or a more-complicated machine such as an automated breast ultrasound (ABUS) machine or a full-body scanner. The image tracking and patching can also be used to correct artifacts created by patient motion (e.g., breathing) and/or transducer compression during the 3D-volume data acquisition. For example, the image patching and 3D high-resolution volume acquisition techniques can be used not only for a simple freehand scan but also for a sophisticated 3D ultrasound scanner, such as ABUS or a full-body scanner.

When moving the transducer 214, the user can be notified of whether the movement is enabling image patching. For example, a first indicator 504 can be provided to notify the user that there is a poor correlation between images being generated from the ultrasound-data acquisition based on the current movement of the transducer 214 and that the images being generated are not being patched together. A second indicator 506 can be provided to notify the user that there is a good correlation between images being generated from the ultrasound-data acquisition based on the current movement of the transducer 214 and that the images are being patched together.

The first and second indicators 504, 506 can be visual indicators, for example, displayed via the display device 108 or provided via an LED on the scanner or another device coupled to the ultrasound system 100. The first and second indicators 504, 506 can be audio signals output by a speaker coupled to, or integrated with, the ultrasound machine 102 or the scanner 104.

The amount of shift can be recorded through image tracking to guide the user to stop movement of the transducer 214 in the lateral direction 410 and begin movement of the transducer 214 in the elevational direction 412, which can avoid gaps in the 3D volume acquisition and/or minimize the number of sweeps. In addition, the amount of shift can also be tracked to guide the user to stop moving the transducer 214 in the elevational direction 412 and begin moving the transducer 214 in the lateral direction 410, which can help the user to align the transducer 214 in-plane with a previous position. For example, a notification (visual, audio, or both) can be provided to the user to instruct the user to stop the elevational movement of the transducer 214 when reaching the fourth transducer position 214-4, such that the fourth transducer position 214-4 is in-plane (xz-plane) with the first transducer position 214-1. Such in-plane positioning can enable image patching of an image generated from the fourth position 214-4 with an image generated at the first position 214-1.

Figure 6:
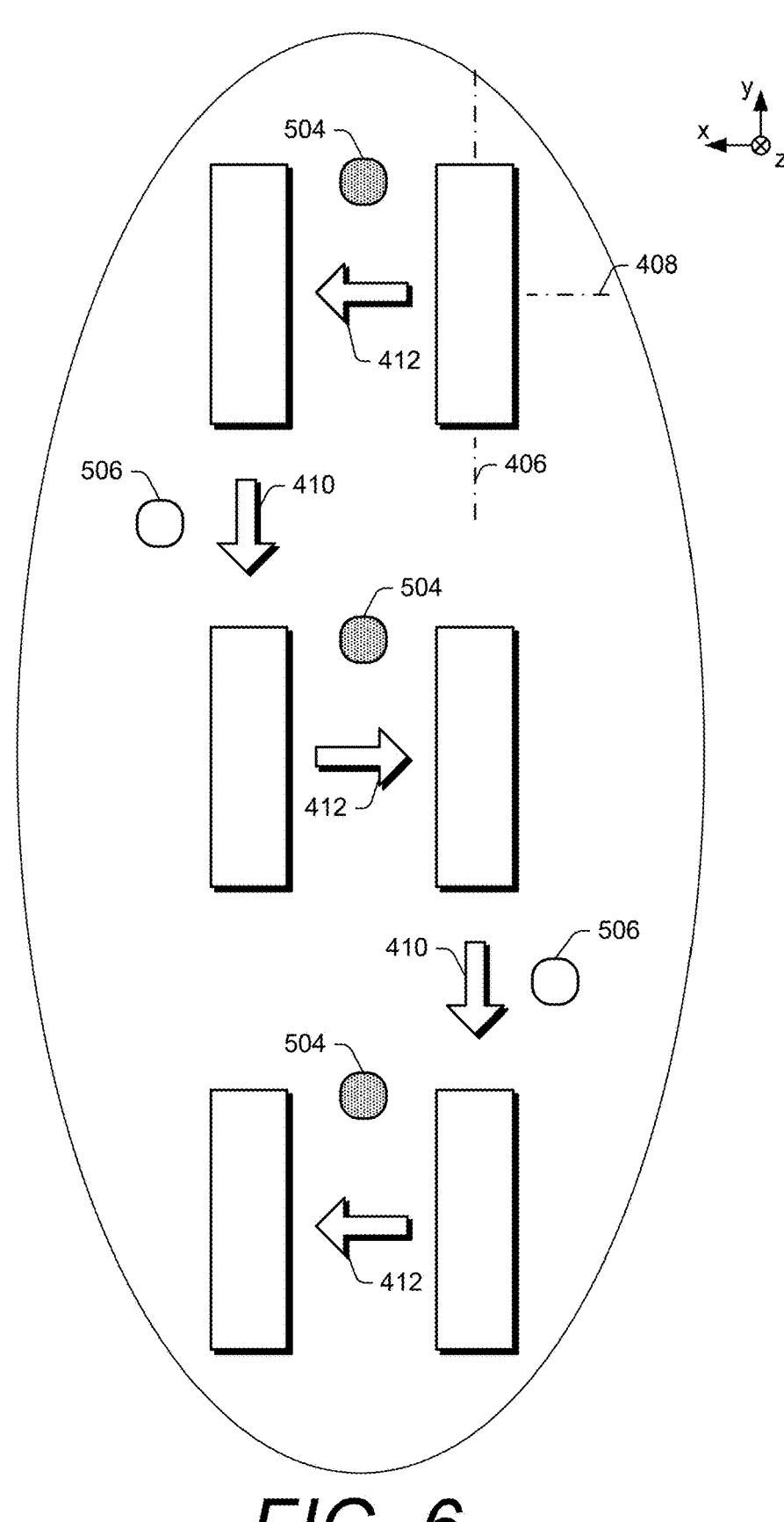
FIG. 6 illustrates an example second sweep pattern for acquisition of a 3D ultrasound volume with a 1D-array transducer using image registration.

FIG. 6 illustrates an example second sweep pattern 600 for acquisition of a 3D ultrasound volume with a 1D-array transducer using image registration. In comparison to the first sweep pattern 500 of FIG. 6, the transducer 214 in the second sweep pattern 600 of FIG. 6 has been rotated approximately 90 degrees. Accordingly, in the second sweep pattern 600, the lateral direction 410 (e.g., parallel to the first axis 406 of the transducer 214) corresponds to the y-axis and the elevational direction 412 (e.g., non-parallel to the first axis 406 of the transducer 214 or substantially parallel to the second axis 408) corresponds to the x-axis.

In the second sweep pattern 600, the transducer is moved along the elevational direction 412 first, followed by movement in the lateral direction 410. Similar to the example shown in FIG. 5, elevational movement of the transducer 214 (along the x-axis in FIG. 6) produces images with a low correlation between neighboring 2D images and the neighboring images cannot be patched together. However, lateral movement of the transducer 214 (along the y-axis in FIG. 6) produces images with a high correlation between neighboring 2D images and the neighboring images can be patched together. As is described with respect to FIG. 5, such high and low correlations can be indicated to the user in real-time as the user is moving the transducer 214.

Like the example described with respect to the first sweep pattern 500 in FIG. 5, the first and second indicators 504, 506 can be provided, as the user moves the transducer 214 through the second sweep pattern 600, to indicate whether images being generated are being patched together or not. Because the transducer 214 has been rotated, now high-resolution images can be patched together along the y-axis, whereas low-resolution images are generated along the x-axis and not patched.

The output volumes from the first sweep pattern 500 and the second sweep pattern 600 can be registered together to create a high-resolution 3D volume. Such a high-resolution 3D volume can be created because the high-resolution direction of the first sweep pattern 500 corresponds to the low-resolution direction of the second sweep pattern 600 (e.g., along the x-axis), whereas the low-resolution direction of the first sweep pattern 500 corresponds to the high-resolution direction of the second sweep pattern 600 (e.g., along the y-axis). A registration between a low-resolution image and a high-resolution image in the volumes created by different sweeps can then be performed to patch the images together and create the high-resolution volume. Accordingly, guiding the user with indicators (e.g., the first and second indicators 504 and 506, respectively) can help the user move the transducer 214 in a manner that acquires a complete volume without gaps. Further, using such guidance can reduce or minimize the number of transducer movements used in the sweep pattern(s) to acquire the ultrasound data for generating the 3D volume.

Figure 7:
FIG. 7 illustrates an example implementation of using ultrasound signals from different angles to view locations under a specular reflector, such as a bone.
Figure 7:
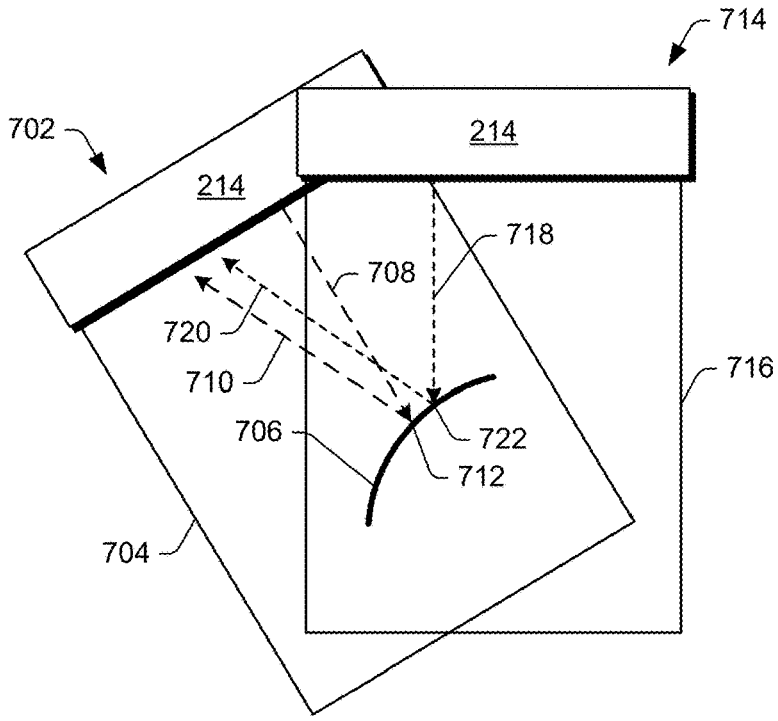

FIG. 7 illustrates an example implementation 700 of using ultrasound signals from different angles to view locations under a specular reflector, such as a bone. During ultrasound scanning, specular reflectors (e.g., bones) can vary intensities as the scanning angle changes. If the ultrasound beam is perpendicular to the bone surface, the reflected intensity is strong. However, when the ultrasound beam encounters the bone surface at a non-perpendicular angle, the ultrasound beam can be deflected away from the transducer, resulting in missing ultrasound signals corresponding to the bone surface. In addition, due to the amount of energy reflected or deflected from the specular reflector, the tissue under the bone surface can be dark in the ultrasound image, resulting in missing ultrasound signals corresponding to soft tissue.

In FIG. 7, for example, the transducer 214 is positioned at a first position 702 and transmits ultrasound signals generally over a depth represented by area 704. When encountering a specular reflector, such as bone 706, the ultrasound signals reflect off the surface of the specular reflector with high intensity, and the area behind the specular reflector remains unscanned. For example, a first ultrasound signal 708 is transmitted by the transducer 214 at the first position 702, and a corresponding reflection 710 of the first ultrasound signal 708 reflects off the surface of the bone 706 at a first point 712. The corresponding reflection 710 is received by the transducer 214 and is processed to indicate a surface of a structure, such as a bone, in a corresponding ultrasound image. Because the bone 706 is a specular reflector, the ultrasound signals do not penetrate the surface of the bone 706 and are instead diverted back to the transducer 214 without providing any information corresponding to the tissue on the opposite side of the reflective surface of the bone 706. Consequently, information underneath the surface of the bone 706 remains unscanned.

In aspects, information corresponding to the same location can be tracked to enable some information to be overridden by more accurate information. In the illustrated example, the transducer 214 is subsequently tilted to a second position 714 and scans area 716, which overlaps the area 704 scanned from the first position 702. At the second position 714, some of the ultrasound signals reflect away from the transducer 214 due to the non-perpendicular angle at which the ultrasound signals encounter the surface of the bone 706. For example, a second ultrasound signal 718 is transmitted by the transducer 214 at the second position 714, and a corresponding reflection 720 of the second ultrasound signal 718 reflects off the surface of the bone 706 at a second point 722, which is near (or the same) point as the first point 712. Due to the angle at which the second ultrasound signal 718 encounters the surface of the bone 706, the transducer 214 does not receive the corresponding reflection 720. Without detecting the reflection 720, the ultrasound system 100 can incorrectly determine that the tissue at the second point 722 does not reflect ultrasound signals, along with the area below the first point 712. When patching ultrasound images using conventional techniques, subsequently acquired ultrasound data is used to overwrite previously acquired ultrasound data. Consequently, using such conventional techniques, some of the surface of the bone 706 detected by the transducer 214 in the first position 702 in this example can be overwritten by the lack of reflections (e.g., reflection 720) detected at those same points by the transducer 214 in the second position 714, resulting in a false dark area in the ultrasound image.

Using the techniques disclosed herein, angle information of each acquired image is recorded. The variation of intensities among different images can be detected and analyzed. If the same location at different angles has a large variation in intensity (greater than 10%, 20%, 25%, etc.), the tissue at that location can be detected as being a specular reflector or reflection border. By tracking the location at different angles, a greater value (e.g., maximum) for that location from the different angles can be used to generate the ultrasound image. An example comparison of ultrasound images is shown in FIG. 8 to illustrate expected results using conventional techniques versus using the techniques disclosed herein.

Figure 8:
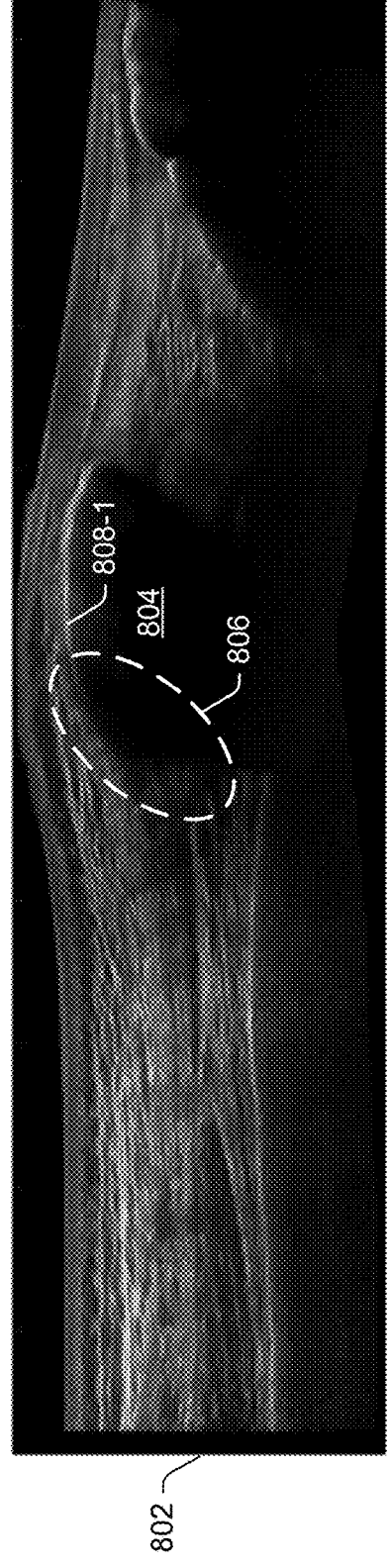
FIG. 8 shows an example comparison between an ultrasound image generated using the techniques disclosed herein compared to an ultrasound image generated using conventional techniques.
Figure 8:
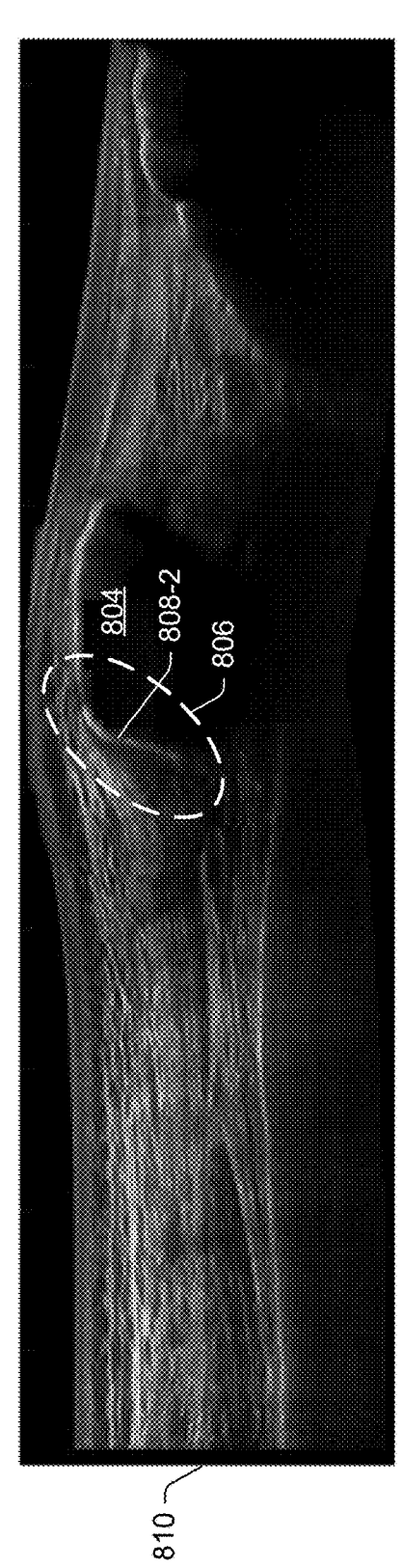

FIG. 8 shows an example comparison 800 between an ultrasound image generated using the techniques disclosed herein compared to an ultrasound image generated using conventional techniques. For example, a first ultrasound image 802 is a conventional panoramic ultrasound image generated from left to right as the scanner moves across the patient anatomy. When the conventional scan encounters a bone structure 804, patching is performed by using a most-recent frame to override a previous frame, which causes a portion 806 of the bone structure 804 to disappear. Note how the bone surface (represented by bright pixels 808-1) is missing in the portion 806 of the bone structure 804. Accordingly, the most-recent frame might not be the best frame because it could have missing bone information underneath due to the reflection.

In comparison to the first ultrasound image 802, a second ultrasound image 810 is an ultrasound image generated using the techniques disclosed herein over the same patient anatomy as the first ultrasound image 802. Note how the bone surface (e.g., bright pixels 808-2) are included in the portion 806 of the bone structure 804. When the scanner passes over the bone structure 804 from left to right, the top surface of the bone structure 804 blocks the information underneath so the signal is lost, similar to the conventional scan. However, using the disclosed techniques, a large variation of the intensity at the same location is detected (e.g., from bright to dark). This intensity variation is an indication that there is hidden information that the bone surface is blocking. Based on, or in response to, detecting the intensity variation, the ultrasound system 100 can maintain or use the greater intensity values at each location that has the variation. Using the greater intensity values can provide more-accurate information in the ultrasound image, such as the surface of a bone (e.g., the bright pixels 808-2 in the portion 806 of the bone structure 804), and provide minimal loss of information in the scan.

Figure 9A:
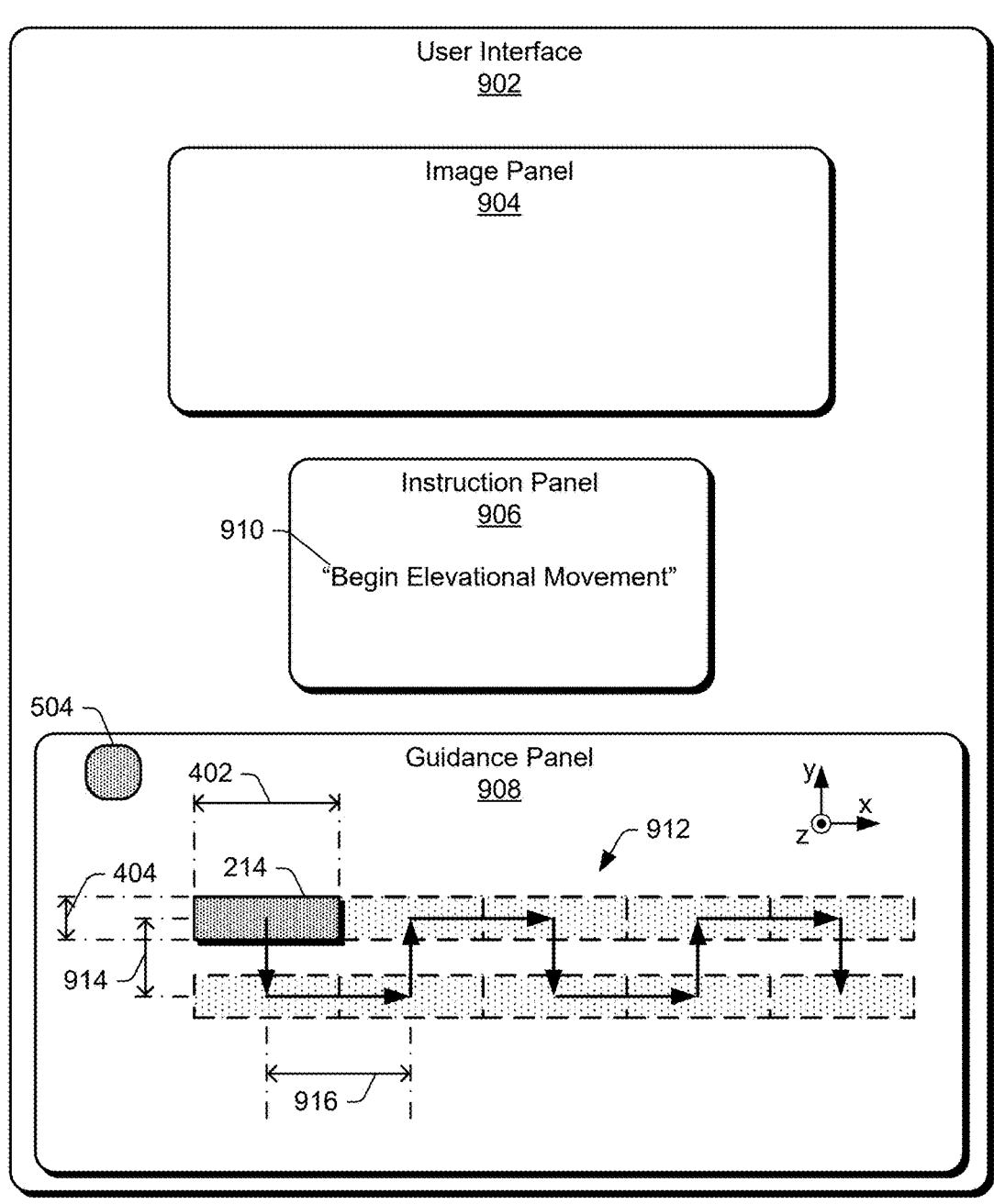
FIGS. 9A and 9B illustrate example implementations of a user interface displayable via a display device to guide a user in manually moving the transducer in one or more sweep patterns to collect ultrasound data sufficient to produce a 3D ultrasound volume and avoid gaps (missing portions) in the data.
Figure 9B:
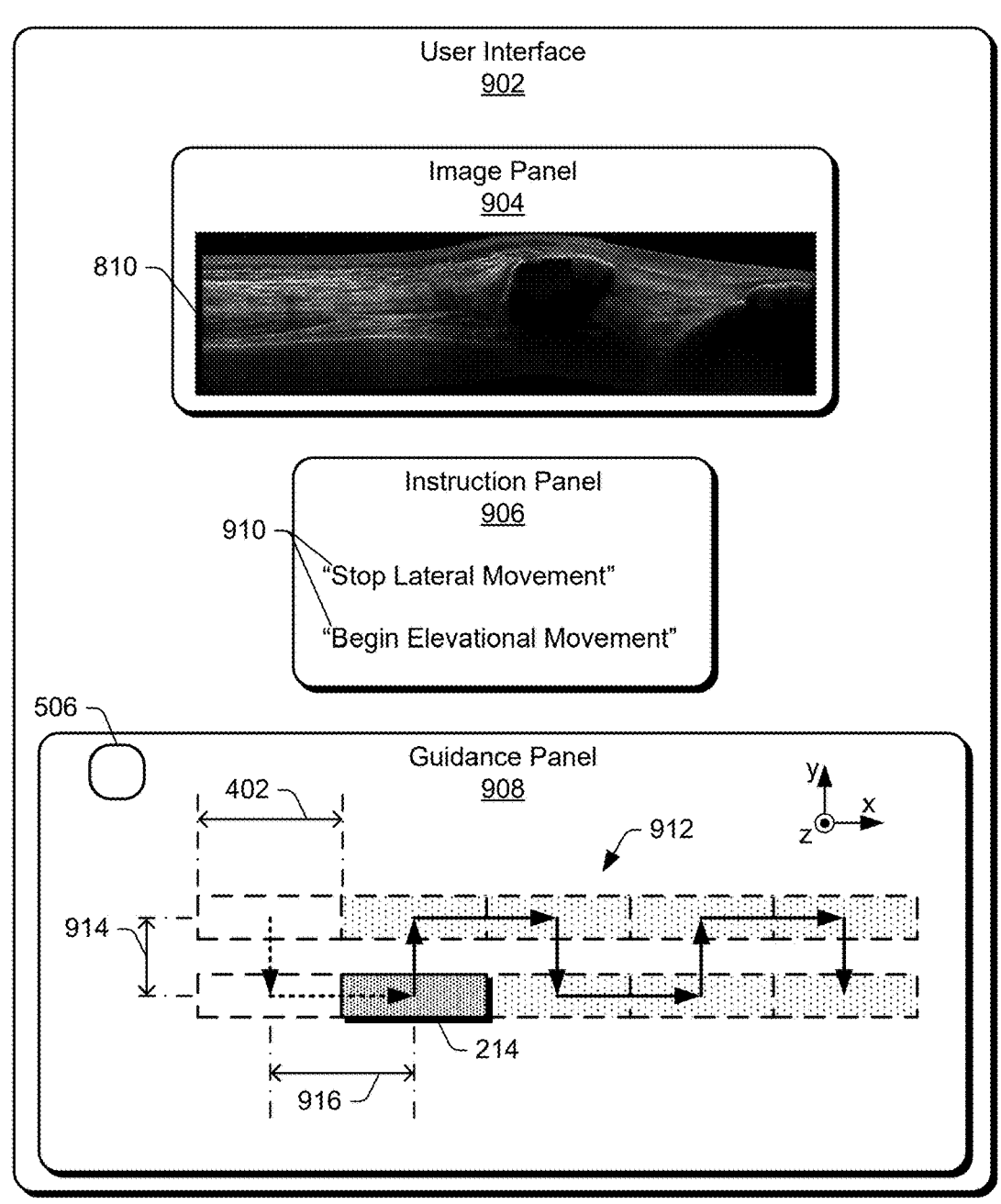

FIGS. 9A and 9B illustrate example implementations 900 and 950, respectively, of a user interface 902 displayable via a display device to guide a user in manually moving the transducer in one or more sweep patterns to collect ultrasound data sufficient to produce a 3D ultrasound volume and avoid gaps (missing portions) in the data. For example, the user interface 902 can be rendered via the display device 108 during an ultrasound scanning procedure of the patient anatomy. The user interface 902 can present the guidance information 324 (shown in FIG. 3), which can include instructions for manually moving the transducer 214 specific distances and directions to cover an area of the patient anatomy in a manner that enables the ultrasound system 100 to produce panoramic ultrasound images and the 3D volume. In some implementations, the user interface 902 can include a plurality of panels, such as an image panel 904, an instruction panel 906, and a guidance panel 908. The user interface 902 can include one or more additional panels, such as panels for displaying user-selectable controls, operation parameters, etc. for controlling operation of the scanner 104 or to influence data acquisition.

In one example, guidance instructions 910 can be shown in the instruction panel 906 in text or typed form. The guidance instructions 910 can also or alternatively be provided as audio instructions output via a speaker. The guidance panel 908 can include a suggested sweep pattern 912, such as a diagram showing directions, distances, and/or locations to move the transducer 214 over the patient anatomy. With the transducer 214 at a starting location (e.g., top left position of the diagram), the guidance instructions 910 can notify the user to "begin elevational movement" of the scanner 104. In addition, the suggested sweep pattern 912 can visually indicate to the user to shift the transducer 214 in the elevational direction (e.g., parallel to the width of the transducer). By tracking one or more of the spatial position, acceleration, angle, elevation, etc. of the transducer 214, the ultrasound system 100 can provide real-time positioning of the transducer relative to the suggested sweep pattern 912. Further, the ultrasound system 100 can monitor the distance traveled by the transducer 214, such as a first distance 914 in the elevational direction, a second distance 916 in the lateral direction, etc.

The first distance 914 can be any suitable distance. As described herein, ultrasound data acquired in the elevational direction is not patched together but is stored in frames side-by-side to create a volume. In some implementations, the first distance 914 can be any suitable distance; however, the frames generated in the elevational direction have low resolution. The second distance 916 can be any suitable distance. In some cases, the patching provides an indication of a distance to laterally move the transducer 214 to avoid missing a portion of the information being collected to create the 3D volume. Such an indication can correspond to the length of the transducer 214 or a width of an ultrasound frame generated at a first location of lateral movement of the transducer 214. In one example, the second distance 916 is substantially equal to the length 402 of the transducer 214 (2.5 centimeters (cm), 3 cm, 5 cm, etc.). However, the second distance 916 can be less than the length 402 to retain some overlap between a first frame taken along the lateral movement and a last frame taken along the lateral movement to reduce the risk of gaps in the ultrasound data when subsequently moving the transducer 214 in the elevational direction. If the second distance 916 is greater than the length 402, then the sweep pattern can be adjusted dynamically to guide the user to move the transducer over any gaps or missing ultrasound data in the resulting volume.

Continuing the example with FIG. 9B, as the user moves the transducer 214 in the lateral direction, the guidance instructions 910 can instruct the user to "stop lateral movement" and "begin elevational movement." In addition, the suggested sweep pattern 912 can show a real-time position of the transducer 214 relative to the suggested sweep pattern 912 and provide an indication (arrow, highlight, color, size, brightness change, etc.) of a new direction to move the transducer 214, such as the elevational direction. Further instructions can be provided to the user to, for example, stop elevational movement and begin lateral movement, move the transducer left, move the transducer right, move the transducer slower, move the transducer faster, rotate the transducer and begin lateral or elevational movement, stop movement of the transducer because the sweep pattern is complete, etc. The suggested sweep pattern 912 can emphasize or de-emphasize portions of the sweep pattern to indicate a current location, past locations, and/or suggested future locations of the transducer 214 along the sweep pattern.

As the transducer 214 is moved in the lateral direction, the user interface 902 can also provide indications (e.g., the first indicator 504, the second indicator 506) to notify the user whether the movement of the transducer is resulting in a poor correlation between ultrasound image frames such that the frames cannot be patched together or a good correlation between ultrasound image frames such that the frames can be patched together.

The image panel 904 can provide a panoramic ultrasound image, generated using image registration of the ultrasound data acquired or generated according to the movement of the transducer 214 in the one or more sweep patterns. In some implementations, the image panel 904 can provide a partial panoramic image during the movement of the transducer 214 and enlarge the panoramic image as more ultrasound data is collected and patched to it. In other implementations, the image panel 904 shows the panoramic image only after the transducer movement completes one or more sweep patterns. Alternatively, the image panel 904 can provide an ultrasound image corresponding to the current position of the transducer 214 in real time.

After the transducer movement completes the suggested sweep pattern 912, in some aspects, the user interface 902 can provide one or more additional suggested sweep patterns, such as the second sweep pattern 600 in FIG. 6, to enable acquisition of high-resolution ultrasound images in a different direction than that of the suggested sweep pattern 912. For example, following the second sweep pattern 600 can provide high-resolution ultrasound data along the y-axis, which can be combined (e.g., patched) with the low-resolution ultrasound data acquired along the y-axis in the suggested sweep pattern 912. Using tracking and image registration, the ultrasound data from multiple sweep patterns can provide a high-resolution 3D volume for panoramic imaging.

Tracking and Patching Ultrasound Frames

Any suitable tracking method can be utilized to track the ultrasound data. In one implementation, image patching can determine the minimum difference between two image frames. For example, the ultrasound system 100 can calculate a transform matrix for each angle, x-offset, and y-offset. Based on the transformation matrix, the ultrasound system 100 can compute a P2 point from the second frame, which represents a point or pixel in the second frame in the same location of the patient anatomy as a P1 point or pixel in the first frame. Then, the sum of absolute difference (SAD) error can be measured between P1 and P2 and the resulting output can be recorded as the transformation that has the minimum SAD value between the given frames.

After the angles and translations are determined, the angle and the x-and y-translations corresponding to the minimum SAD value are recorded. If the resulting SAD value is less than a predefined threshold and the translation is reasonably large, then the difference between the frames can be considered lateral movement (with or without rotation) of the transducer 214 and image patching can be performed. If the resulting SAD value is less than a predefined threshold and the translation is small, then the difference between the frames can be considered to be nominal or negligible and the second frame is not stored in the volume. If the resulting SAD value is greater than the predefined threshold and there is no clear translation, then the difference between the frames can be considered elevational movement (with or without rotation) of the transducer 214 and the image is stored in a different frame.

The transformation matrix can be represented using the following rotation and translation matrix, based on the soft tissue being considered rigid:

$$\text{RotationMatrix} = \begin{bmatrix} \cos\theta & -\sin\theta & x \\ \sin\theta & \cos\theta & y \\ 0 & 0 & 1 \end{bmatrix} \qquad \text{Equation (1)}$$

If no rotation is detected, then Equation (1) can be a simple translation matrix for x-and y-translations, thereby reducing the amount of computation and decreasing the processing time for tracking the distance of motion. Other example tracking methods that can be used to track the ultrasound frames include cross correlation, feature extraction, etc. Accordingly, any suitable tracking method can be used to track the ultrasound frames. The techniques disclosed herein use the tracking information to guide the user to manually move the transducer to enable acquisition of a 3D volume of ultrasound data. The acquired ultrasound data can be subsequently sent to a medical professional or a machine-learned model for analysis. In this way, a conventional scanner can be used to acquire the ultrasound data without requiring additional hardware.

In some implementations, image tracking is implemented during the lateral movement of the transducer 214 and not during elevational movement of the transducer 214 because frames can be patched when in-plane with one another. Out-of-plane frames can be stored side-by-side based on acquisition times (e.g., timestamps).

In some implementations, the image tracking and/or image patching can automatically start or stop based on transducer movement. For example, if lateral movement of the transducer 214 is detected, then tracking and patching can be automatically initiated. If the tracking and patching are active and elevational movement of the transducer 214 is detected, then the tracking and patching can be automatically stopped.

The image tracking can be sensor-based tracking. For example, sensor information can be tracked to determine if the transducer is moved laterally or elevationally and image patching can then be initiated or ceased, respectively. In some cases, if lateral movement of the transducer 214 is detected, the ultrasound system 100 can provide a prompt to the user that asks if the user wants to see a panoramic image. If a user input, responsive to the prompt, confirms that a panoramic image is desired, then image patching can be initiated to generate the panoramic image for presentation via the user interface 902. If the user input declines the panoramic image, then image patching is not initiated.

Example Methods

Figure 10:
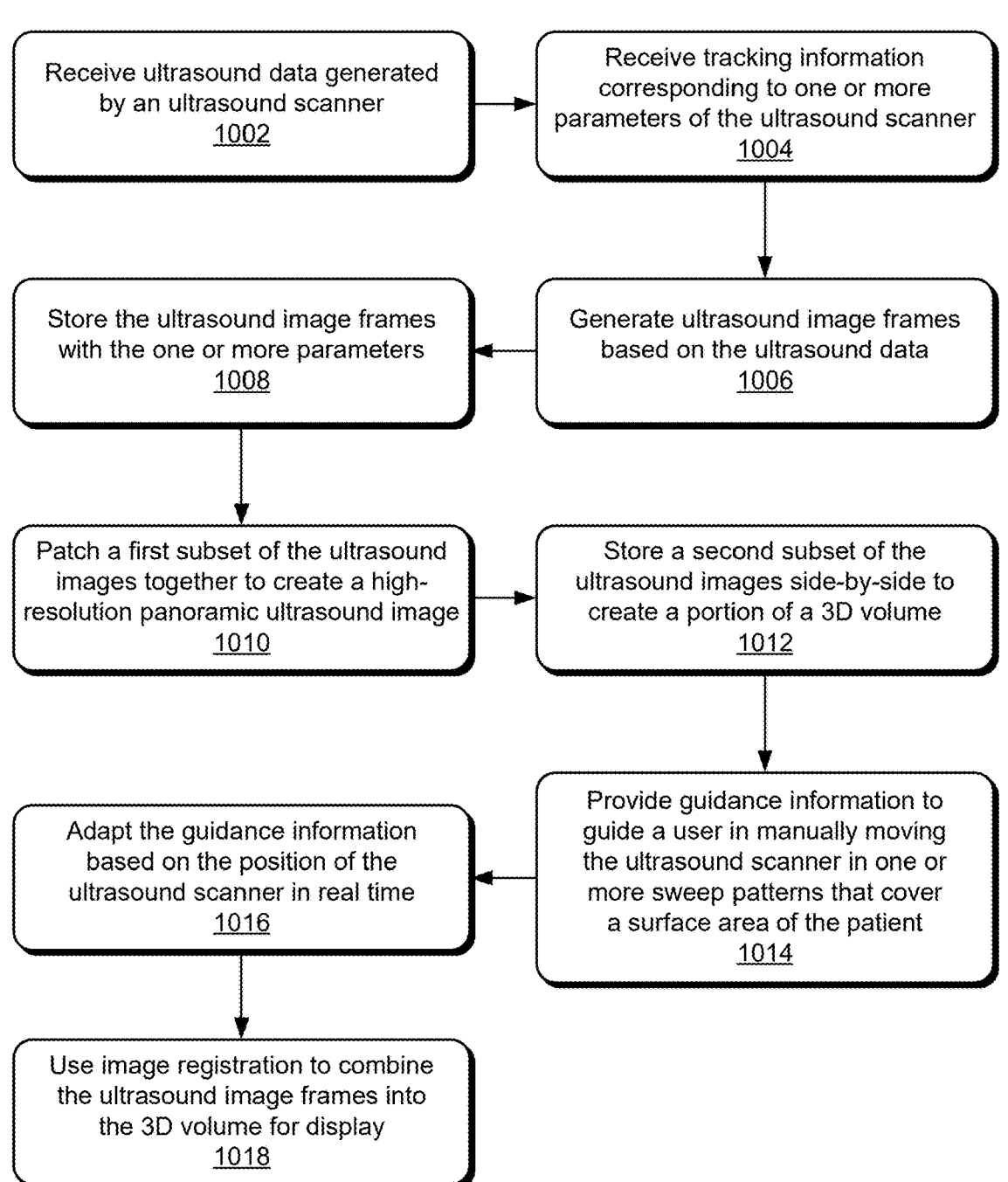
FIGS. 10 depicts a method for panoramic imaging in 2D and 3D ultrasound images, in accordance with one or more implementations.

FIG. 10 depicts a method 1000 for panoramic imaging in 2D and 3D ultrasound images. The method 1000 is shown as a set of blocks that specify operations performed but are not necessarily limited to the order or combinations shown for performing the operations by the respective blocks. Further, any of one or more of the operations can be repeated, combined, reorganized, or linked to provide a wide array of additional and/or alternate methods. In portions of the following discussion, reference can be made to the example ultrasound system 100 of FIG. 1 or to entities or processes as detailed in FIGS. 2-9, reference to which is made for example only. The techniques are not limited to performance by one entity or multiple entities operating on one device.

At 1002, ultrasound data, generated by an ultrasound scanner based on reflections of ultrasound signals transmitted by the ultrasound scanner at an anatomy of a patient, is received. In an example, the processor system 314 receives the scan data 304 from the scanner 104 based on ultrasound signals transmitted by the scanner 104 at the patient anatomy 302. The scanner 104 includes the transducer 214, which has a length 402 and a width 404 that define a plane. The transducer has a first axis (e.g., the first axis 406) along the length 402, a second axis (e.g., the second axis 408) along the width 404, and a third axis along an axial direction of the transducer 214.

At 1004, tracking information, corresponding to one or more parameters associated with the ultrasound scanner when the ultrasound signals are transmitted by the ultrasound scanner, is received. The tracking information can be generated by the image-tracking module 112 for each ultrasound image frame. In aspects, the tracking information includes one or more parameters of the transducer 214 when the ultrasound data (e.g., the scan data 304) is generated. In some examples, the image-tracking module 112 can generate the tracking information based on sensor information provided by the sensor 310, which can be integrated with or communicatively coupled to the scanner 104.

At 1006, ultrasound image frames are generated based on the ultrasound data. For example, the processor system 314 generates an ultrasound image from the scan data 304 generated by the scanner 104.

At 1008, the ultrasound image frames are stored with the one or more parameters. For example, the ultrasound-image data, including the ultrasound image frames, are stored in the database 318 along with the tracking information and/or sensor data 312. The parameters can include at least one of a position, an acceleration, an angle, or an elevation of the transducer 214.

At 1010, a first subset of the ultrasound-image frames are patched together to create a high-resolution panoramic ultrasound image. The first subset is generated based on the ultrasound scanner moving in a lateral direction. The lateral direction is defined as movement of the ultrasound scanner in a first direction that is parallel to a longitudinal axis of a transducer of the ultrasound scanner. In aspects, the longitudinal axis is the first axis 406 of the transducer 214. In an example, the image-patching module 114 patches ultrasound images together that are generated during the lateral movement of the transducer 214 to provide one or more 2D panoramic images.

At 1012, a second subset of the ultrasound image frames are stored side-by-side to create a portion of the 3D volume. The second subset is generated when the ultrasound scanner moves in an elevational direction. The elevational direction is defined as movement of the transducer in a second direction that is non-parallel to the longitudinal axis of the transducer. In some aspects, the elevational direction is substantially aligned with the second axis 408 of the transducer 214. In an example, the elevational movement can be defined as movement of the scanner 104 that is out-of-plane with the first axis 406 and the second axis 408.

At 1014, guidance information is provided to guide a user in manually moving the ultrasound scanner in one or more sweep patterns that cover a surface area of the patient, the guidance information including instructions for moving the ultrasound scanner in different directions over the one or more sweep patterns. In an example, the guidance information is provided in a user interface displayed via a display device. The sweep pattern can include the lateral movement and the elevational movement of the ultrasound scanner 104 over the anatomy.

The guidance information can be provided via the LED 222, which can be coupled to, or integrated with, the scanner 104 or the ultrasound machine 102. For example, the guidance information (e.g., instructions) can be provided in the form of color, brightness level, flash pattern, or size of the LED 222. In some aspects, the guidance information is provided as audio signals output via the speaker 224. Additionally or alternatively, the guidance information can be provided as one or more visual objects rendered via the user interface 902 displayed via the display device 108. The guidance information can include guidance indicators (e.g., indicators 504 and 506) that verify to the user that the ultrasound transducer is moving at a speed that is within a threshold range of movement speed for patching ultrasound images, or that notify the user that the ultrasound transducer 214 is moving at a speed that is outside the threshold range of movement speed for patching ultrasound images. In aspects, the guidance information can notify the user (i) during lateral movement of the ultrasound scanner 104 in the sweep pattern that the ultrasound system 100 is patching ultrasound images generated from the ultrasound data being generated and/or (ii) during elevational movement of the ultrasound transducer 214 in the sweep pattern that the ultrasound system 100 is not patching ultrasound images generated from the ultrasound data being generated.

In an example, the guidance information includes a diagram of the suggested sweep pattern 912 for the user to follow in manually moving the transducer 214, where the diagram is displayed via the guidance panel 908 of the user interface 902. The diagram can include a plurality of locations and directions in which to move the transducer 214 to cover the surface area of the patient. The user interface 902 can also include the image panel 904 configured to display one or more panoramic ultrasound images (e.g., the second ultrasound image 810) generated from the ultrasound data (e.g., the scan data 304) that is generated over the sweep pattern, where the one or more panoramic ultrasound images are generated by patching ultrasound frames generated during the lateral movement of the transducer 214.

At 1016, the guidance information is adapted based on the position of the ultrasound scanner in real time. For example, the guidance panel 908 of the user interface 902 can include a representation of a current position of the transducer 214 relative to the suggested sweep pattern 912 in real time. If the user moves the transducer 214 in a manner that diverges from the suggested sweep pattern 912, the guidance information can be adapted to account for the divergence and guide the user to move the transducer 214 in a manner that covers the surface area of the patient and avoids missing portions of the resulting volume.

At 1018, image registration is used to combine the ultrasound image frames into the 3D volume. In an example, the image-patching module 114 uses the image registration to patch first ultrasound images generated during the first sweep pattern with second ultrasound images generated during a second sweep pattern to create the 3D volume with high resolution. In aspects, the first sweep pattern 500 includes first lateral movements and first elevational movements of the ultrasound transducer 214 that cover a first surface area of the patient, while the second sweep pattern

600 includes second lateral movements and second elevational movements of the ultrasound transducer that together cover a second surface area of the patient that overlaps the first surface area. The transducer can be rotated about the third axis (z-axis) in the second sweep pattern 600 relative to the first sweep pattern 500. Further, the first ultrasound images include first high-resolution images generated along the first lateral movements in the first sweep pattern and first low-resolution images generated along the first elevational movements in the first sweep pattern 500. In addition, the second ultrasound images include second high-resolution images generated along the second lateral movements in the second sweep pattern 600 and second low-resolution images generated along the second elevational movements in the second sweep pattern 600. The image-patching module 114 is configured to use the image registration to patch the first high-resolution images with the second low-resolution images and patch the first low-resolution images with the second high-resolution images to create the 3D volume with high resolution.

CONCLUSION

Embodiments of panoramic imaging in 2D and 3D ultrasound images are disclosed are advantageous, as they enable generation of a high-resolution 3D ultrasound volume using image registration. The techniques disclosed herein use image tracking image patching in an intelligent way to reduce processing power and computation time when patching ultrasound images together to form 2D panoramic images and when combining ultrasound images to form the 3D ultrasound volume.

What is claimed is:

1. An ultrasound system comprising:

an ultrasound scanner configured to generate ultrasound data based on reflections of ultrasound signals transmitted by the ultrasound scanner at an anatomy of a patient, the ultrasound scanner including a transducer having a width and a length, the length being greater than the width, the transducer having a first axis along the length, a second axis along the width, and a third axis in an axial direction of the transducer;

a guidance controller configured to provide guidance instructions for manual movement of the transducer, the guidance instructions indicating a sweep pattern over a surface area of the patient, the sweep pattern including lateral movement and elevational movement of the transducer, the lateral movement being defined as movement of the transducer in a lateral direction that is substantially parallel to the first axis of the transducer, the elevational movement being defined as movement of the transducer in an elevational direction that is substantially parallel to the second axis, the guidance controller configured to:

during the lateral movement of the transducer in the sweep pattern, generate a first notification responsive to a determination that ultrasound images generated from the ultrasound data being generated are being patched together and that patched ultrasound images are being generated; and during the elevational movement of the transducer in the sweep pattern, generate a second notification responsive to a determination that ultrasound images generated from the ultrasound data being generated are not being patched together and that unpatched ultrasound images are being generated;

one or more processors; and one or more computer-readable storage media having instructions stored thereon that, responsive to execution by the one or more processors, cause the one or more processors to:

generate a plurality of two-dimensional (2D) ultrasound images based on the ultrasound data generated over the sweep pattern, the plurality of 2D ultrasound images including the patched ultrasound images and the unpatched ultrasound images; and combine the plurality of 2D ultrasound images into a 3D volume using image registration.

2. The ultrasound system of claim 1, further comprising a light-emitting diode (LED) coupled to the ultrasound scanner, wherein the guidance instructions are provided via the LED.

3. The ultrasound system of claim 1, further comprising a speaker, wherein the guidance instructions are provided as one or more audio signals output via the speaker.

4. The ultrasound system of claim 1, further comprising a display device, wherein the guidance instructions include one or more visual objects rendered via a user interface displayed via the display device.

5. The ultrasound system of claim 1, wherein the guidance instructions include:

one or more guidance indicators configured to verify to a user that the transducer is moving at a speed that is within a threshold range of movement speed for patching ultrasound images; and one or more additional guidance indicators configured to notify the user that the transducer is moving at a speed that is outside the threshold range of movement speed for patching ultrasound images.

6. The ultrasound system of claim 1, further comprising a user interface, the user interface including a guidance panel for displaying a diagram of the sweep pattern, the diagram of the sweep pattern including a plurality of locations and directions for the manual movement of the transducer to cover the surface area of the patient.

7. The ultrasound system of claim 1, wherein the instructions further comprising cause the one or more processors to:

generate tracking information for each ultrasound image of the plurality of 2D ultrasound images, the tracking information including one or more parameters of the transducer when generating a respective 2D ultrasound image of the plurality of 2D ultrasound images, wherein:

the image registration includes the tracking information; and the patched ultrasound images include 2D panoramic images.

8. The ultrasound system of claim 2, wherein the guidance instructions correspond to at least one of color, brightness level, flash pattern, or size of the LED.

9. The ultrasound system of claim 6, wherein the guidance panel includes a representation of a position of the transducer relative to the sweep pattern in real time.

10. The ultrasound system of claim 6, wherein the user interface includes an image panel configured to display one or more of the 2D ultrasound images.

11. The ultrasound system of claim 10, wherein the one or more ultrasound images include a panoramic ultrasound image generated by patching ultrasound frames generated during the lateral movement of the transducer.

12. The ultrasound system of claim 7, further comprising a sensor coupled to the ultrasound scanner, wherein the instructions further cause the one or more processors to generate the tracking information based on sensor information provided by the sensor.

13. The ultrasound system of claim 7, wherein the one or more parameters of the transducer include at least one of a position, an acceleration, an angle, or an elevation of the transducer.

14. The ultrasound system of claim 7, wherein:

the sweep pattern is a first sweep pattern;

the surface area is a first surface area of the patient;

the plurality of 2D ultrasound images includes first ultrasound images generated during the first sweep pattern;

the instructions further cause the one or more processors to use the image registration to patch the first ultrasound images generated during the first sweep pattern with second ultrasound images generated during a second sweep pattern to create the 3D volume with high resolution;

the first sweep pattern includes first lateral movements and first elevational movements of the transducer that together cover the first surface area of the patient;

the second sweep pattern includes second lateral movements and second elevational movements of the transducer that together cover a second surface area of the patient that overlaps the first surface area; and the transducer is rotated about the third axis in the second sweep pattern relative to the first sweep pattern.

15. The ultrasound system of claim 14, wherein:

the first ultrasound images include first high-resolution images generated along the first lateral movements in the first sweep pattern and first low-resolution images generated along the first elevational movements in the first sweep pattern;

the second ultrasound images include second high-resolution images generated along the second lateral movements in the second sweep pattern and second low-resolution images generated along the second elevational movements in the second sweep pattern; and the instructions further cause the one or more processors to use the image registration to patch the first high-resolution images with the second low-resolution images and patch the first low-resolution images with the second high-resolution images to create the 3D volume with high resolution.

16. One or more non-transitory computer-readable storage media having instructions stored thereon, that, responsive to execution by one or more processors of an ultrasound system, cause the one or more processors to perform operations comprising:

generating ultrasound data based on reflections of ultrasound signals transmitted by an ultrasound scanner at an anatomy of a patient, the ultrasound scanner including a transducer having a width and a length, the length being greater than the width, the transducer having a first axis along the length, a second axis along the width, and a third axis in an axial direction of the transducer;

providing guidance instructions for manual movement of the transducer, the guidance instructions indicating a sweep pattern over a surface area of the patient, the sweep pattern including lateral movement and elevational movement of the transducer, the lateral movement being defined as movement of the transducer in a lateral direction that is substantially parallel to the first axis of the transducer, the elevational movement being defined as movement of the transducer in an elevational direction that is substantially parallel to the second axis;

during the lateral movement of the transducer in the sweep pattern, generating a first notification responsive to determining that ultrasound images generated from the ultrasound data being generated are being patched together and that patched ultrasound images are being generated;

during the elevational movement of the transducer in the sweep pattern, generating a second notification responsive to determining that ultrasound images generated from the ultrasound data being generated are not being patched together and that unpatched ultrasound images are being generated;

generating a plurality of two-dimensional (2D) ultrasound images based on the ultrasound data generated over the sweep pattern, the plurality of 2D ultrasound images including the patched ultrasound images and the unpatched ultrasound images; and combining the plurality of 2D ultrasound images into a 3D volume using image registration.

17. The one or more non-transitory computer-readable storage media of claim 16, wherein providing the guidance instructions includes providing:

illumination via a light-emitting diode (LED) coupled to the ultrasound scanner;

one or more audio signals output via a speaker coupled to the ultrasound scanner; or one or more visual objects rendered via a user interface displayed via a display device coupled to the ultrasound scanner.

18. The one or more non-transitory computer-readable storage media of claim 1, wherein:

the operations further include generating tracking information for each ultrasound image of the plurality of 2D ultrasound images, the tracking information including one or more parameters of the transducer when generating a respective 2D ultrasound image of the plurality of 2D ultrasound images;

the image registration includes the tracking information; and the patched ultrasound images include 2D panoramic images.

19. The one or more non-transitory computer-readable storage media of claim 16, the sweep pattern is a first sweep pattern;

the surface area is a first surface area of the patient;

the plurality of 2D ultrasound images are first ultrasound images generated during the first sweep pattern;

the operations further include using the image registration to patch the first ultrasound images generated during the first sweep pattern with second ultrasound images generated during a second sweep pattern to create the 3D volume with high resolution;

the first sweep pattern includes first lateral movements and first elevational movements of the transducer that together cover the first surface area of the patient;

the second sweep pattern includes second lateral movements and second elevational movements of the transducer that together cover a second surface area of the patient that overlaps the first surface area; and the transducer is rotated about the third axis in the second sweep pattern relative to the first sweep pattern.

20. The one or more non-transitory computer-readable storage media of claim 18, wherein the tracking information is generated based on sensor information provided by a sensor coupled to the ultrasound scanner.

* * * * *